US012558314B1

(12) United States Patent (10) Patent No.: US 12,558,314 B1
Dhuppad et al. (45) Date of Patent: Feb. 24, 2026

(54) PRESSURIZED INHALATION COMPOSITION OF TIOTROPIUM

(71) Applicant: GLENMARK SPECIALTY S.A., Neuchatel (CH)

(72) Inventors: Ulhas Dhuppad, Navi Mumbai (IN); Raveendra Pai, Navi Mumbai (IN); Ramakant Chanagare, Nashik (IN); Rakshit Trivedi, Nashik (IN); Jitendra Patil, Nashik (IN)

(73) Assignee: GLENMARK SPECIALTY S.A., Neuchatel (CH)

( * ) Notice: Subject to any disclaimer, the term of this patent is extended or adjusted under 35 U.S.C. 154(b) by 0 days.

(21) Appl. No.: 18/969,037

(22) Filed: Dec. 4, 2024

Related U.S. Application Data

(63) Continuation of application No. PCT/IB2024/060352, filed on Oct. 20, 2024.

(30) Foreign Application Priority Data

Aug. 26, 2024 (IN) .............................. 202421064341

(51) Int. Cl.
| | |
|---|---|
| *A61K 9/00* | (2006.01) |
| *A61K 31/439* | (2006.01) |
| *A61K 47/10* | (2017.01) |
| *A61K 47/12* | (2006.01) |
| *A61M 15/00* | (2006.01) |

(52) U.S. Cl.
CPC ............ *A61K 9/008* (2013.01); *A61K 31/439* (2013.01); *A61K 47/10* (2013.01); *A61K 47/12* (2013.01); *A61M 15/0001* (2014.02); *A61M 15/0071* (2014.02)

(58) Field of Classification Search
CPC ...... A61K 9/008; A61K 31/439; A61K 47/10; A61K 47/12; A61M 15/0001; A61M 15/0071
See application file for complete search history.

(56) References Cited

U.S. PATENT DOCUMENTS

| | | | |
|---|---|---|---|
| 2021/0260310 A1* | 8/2021 | Slowey | .................. A61K 47/10 |
| 2022/0257878 A1* | 8/2022 | Berry | .................. A61M 15/002 |

FOREIGN PATENT DOCUMENTS

| | | | |
|---|---|---|---|
| EP | 2606891 A1 | 6/2013 |
| WO | 2004054580 A1 | 7/2004 |
| WO | 2013127738 A1 | 9/2013 |
| WO | 2017075018 A1 | 5/2017 |
| WO | 2020006017 A1 | 1/2020 |

* cited by examiner

*Primary Examiner* — Mina Haghighatian
(74) *Attorney, Agent, or Firm* — Blank Rome LLP

(57) ABSTRACT

A pressurized inhalation composition includes tiotropium or its pharmaceutically acceptable salt thereof, ethanol, a stabilizer, and a propellant. The ethanol can be in an amount of from about 1% (w/w) to about 10% (w/w) based on the total weight of the pressurized inhalation composition. The composition can be pharmacokinetically bioequivalent to non-pressurized aqueous base inhalation formulation of tiotropium. An inhaler can include the composition contained in a canister fitted with metering valve, and an actuator optionally connected with a dose counter. A process of preparing the pressurized inhalation composition and using the pressurized inhalation composition in the treatment of Asthma and Chronic obstructive pulmonary disease (COPD) in a patient in need thereof by inhalation administration are also described.

30 Claims, 2 Drawing Sheets

PRESSURIZED INHALATION COMPOSITION OF TIOTROPIUM

CROSS REFERENCE TO RELATED APPLICATIONS

This application is a continuation of International Application No. PCT/IB2024/060352 filed on Oct. 22, 2024, which claims the benefit of Indian Provisional Application No. 202421064341 filed on Aug. 26, 2024; which is hereby incorporated by reference in its entirety.

TECHNICAL FIELD OF THE INVENTION

The present invention provides a pressurized inhalation composition comprising tiotropium or its pharmaceutically acceptable salt thereof, ethanol, a stabilizer, and a propellant.

The present invention further provides a metered dose inhaler comprising a pressurized inhalation composition comprising tiotropium or its pharmaceutical acceptable salt thereof, ethanol, a stabilizer, and a propellant contained in a canister fitted with metering valve, and an actuator optionally connected with a dose counter. The present invention also relates to a process of preparing said pressurized inhalation composition and its use in the treatment of Asthma and Chronic obstructive pulmonary disease (COPD) in patient in need thereof by inhalation administration.

BACKGROUND OF THE INVENTION

Respiratory diseases are a common and important cause of illness and death around the world. In fact, many people are affected by inflammatory and/or obstructive lung diseases, a category characterized by inflamed and easily collapsible airways, obstruction to airflow, problems exhaling and frequent medical clinic visits and hospitalizations. Types of inflammatory and/or obstructive lung disease include asthma, bronchiectasis, bronchitis and chronic obstructive pulmonary disease (COPD).

A variety of drugs have been developed, including β2-agonists, inhaled corticosteroids and anticholinergics (also referred as muscarinic antagonists or anti-muscarinics) for use in the long-term control of respiratory conditions.

Anticholinergic agents are believed to inhibit vagally-mediated reflexes by blocking acetylcholine at the cholinergic receptor. Anticholinergic agents are also believed to inhibit secretions of the serous and sero-mucous glands of the nasal mucosa. Anticholinergic agents for treatment or control of respiratory disorders include tiotropium, oxitropium, ipratropium, glycopyrrolate and aclidinium or salt thereof.

One known anticholinergic agent is tiotropium bromide, the chemical name of which is, (1α, 2ß, 4ß, 5α, 7ß)-7-[(hydroxydi-2-thienylacetyl) oxy]-9, 9-dimethyl-3-oxa-9-azoniatricyclo[3.3.1.02, 4]nonane bromide monohydrate. Tiotropium bromide is indicated for the maintenance treatment of bronchospasm associated with COPD, and for reducing COPD exacerbations and also for long term maintenance treatment of asthma.

Tiotropium bromide is available commercially in two dosage forms namely—(i) Dry Powder Inhalation under the Brand Name SPIRIVA® Handihaler and; (ii) Soft Mist inhalation solution under the Brand Name SPIRIVA® Respimat. SPIRIVA Handihaler delivers 10 μg tiotropium while SPIRIVA Respimat delivers 5 μg tiotropium as an inhalation dose. SPIRIVA Respimat is available in a special device which is complex in nature and expensive to the patient.

International Publication No. WO 2004/054580 discloses an aerosol solution comprising a tiotropium salt, an HFC propellant, a cosolvent, and an inorganic or organic acid. The concentration of acid is such that it corresponds to pH between 2.5 to 4.5 in aqueous solution.

European patent publication No. EP2819669 discloses pressurized gas preparations containing tiotropium bromide in solution in HFA-propellant gasses as propellant. The solution composition includes propellant HFA134a, mixture of co-solvents i.e. ethanol (15-40% w/w) and water (0.5-2.5% w/w) and acid such that pH is between 6 and 8.

European patent publication No. EP2606891 discloses a solution formulation of a tiotropium salt comprising 12-20% (w/w) of ethanol, 0.1-1.5% (w/w) of water, 0.05-0.10% (w/w) of citric acid and an HFA propellant.

International Publication No. WO 2020/006017 discloses a metered dose inhaler equipped with a metering valve and having canister containing composition comprising tiotropium, wherein the internal surface of canister is coated with a non-metal material composed of silane primer having polyfluoropolymer ether such as fluorinated ethylene propylene (FEP) co-polymer.

European patent application publication no. EP3368083 discloses a composition containing tiotropium, citric acid (between 0.10 and 0.2% w/w), glycerol (0.5-2% w/w), ethanol (up to 20% w/w) and 1,1,1,2-tetrafluoroethane as propellant.

Despite of above stated prior formulation, there still exists a need for a stable pressurized metered dose inhalation composition of tiotropium or its pharmaceutically acceptable salt which can overcome the issues and drawback known in the art and provide effective therapeutic treatment for respiratory diseases like asthma and COPD.

SUMMARY OF THE INVENTION

The present invention relates to a pressurized inhalation composition in a metered dose inhaler comprising tiotropium or its pharmaceutically acceptable salt thereof, ethanol, a stabilizer, and a propellant.

In one embodiment, the present invention relates to a pressurized inhalation composition in a metered dose inhaler comprising tiotropium or its pharmaceutically acceptable salt thereof, ethanol in an amount of from about 1% (w/w) to about 10% (w/w), based on the total weight of the pressurized inhalation composition, a stabilizer, and a propellant.

In one embodiment, wherein the composition in a metered dose inhaler provides a fine particle fraction (FPF) of tiotropium or its pharmaceutically acceptable salt thereof of at least 70%.

In one embodiment, the pressurized inhalation composition is pharmacokinetically bioequivalent to a non-pressurized aqueous base inhalation formulation of tiotropium (e.g., pharmacokinetically bioequivalent to Spiriva Respimat® Inhalation Solution, Eq. 0.0025 mg or 0.00125 mg base/inhalation).

In an another embodiment, the present invention relates to a pressurized inhalation composition wherein the pharmacokinetic bioequivalence is established by (a) 90% confidence interval for AUC which is between 80% and 125%, and (b) 90% confidence interval for $C_{max}$, which is between 80% and 125%.

In an another embodiment, the present invention relates to a pressurized inhalation composition wherein the $C_{max}$ and the AUC of the pressurized inhalation composition is substantially the same as the non-pressurized aqueous base inhalation formulation of tiotropium.

In an embodiment, the pressurized inhalation composition of the present invention is in solution or suspension form. Preferably, the composition is in solution form.

In an embodiment, the tiotropium salt as used in the composition is tiotropium bromide monohydrate.

In an embodiment, the present invention relates to a pressurized inhalation composition wherein the tiotropium bromide monohydrate is in an amount of from about 0.001% (w/w) to about 0.01% (w/w), or from about 0.003% (w/w) to about 0.007% (w/w), or from about 0.005% (w/w) to about 0.006% (w/w), based on the total weight of the pressurized inhalation composition.

In another embodiment, the present invention relates to a pressurized inhalation composition wherein the ethanol is in an amount of from about 5% (w/w) to about 10% (w/w) or from about 8% (w/w) to about 10% (w/w), based on the total weight of the pressurized inhalation composition.

In an embodiment, the ethanol is in amount of about 10% (w/w) based on the total weight of the pressurized inhalation composition.

In an embodiment, the propellant is selected from the group consisting of HFA134a, HFA 227, and any mixture thereof. Preferably, propellant as used in this invention is HFA 134a.

In an another embodiment, the present invention relates to pressurized inhalation composition wherein the weight ratio of the ethanol to the stabilizer is from about 100:1 to about 2:1, or from about 100:1 to about 10:1, or from about 80:1 to about 40:1.

In an embodiment, the pressurized inhalation composition comprises the stabilizer selected from the group consisting of an organic acid, an inorganic acid (or mineral acid), a surfactant, and a chelating agent.

In an embodiment, the stabilizer is selected from the group consisting of citric acid, ascorbic acid, maleic acid, malic acid, hydrochloric acid, phosphoric acid, nitric acid, sulphuric acid and any mixture thereof. Preferably, citric acid is used as stabilizer.

In an embodiment, the present invention relates to pressurized inhalation composition wherein the stabilizer is citric acid present in an amount of from about 0.05% (w/w) to about 0.5% (w/w), or from about 0.08% (w/w) to about 0.35% (w/w), or from about 0.10% (w/w) to about 0.2% (w/w), based on the total weight of the pressurized inhalation composition.

In another embodiment, the pressurized inhalation composition is substantially free of water and glycerol.

In another embodiment, the pressurized inhalation composition is substantially free of anti-oxidant.

In an another embodiment, the present invention relates to a pressurized inhalation composition wherein the pH of the composition is from about 2.5 to about 4.0.

In one of the embodiment, the present invention relates to a pressurized inhalation composition comprising (a) tiotropium bromide monohydrate in an amount of from about 0.0001% (w/w) to about 0.01% (w/w) based on the total weight of the pressurized inhalation composition; (b) ethanol in an amount of from about 1% (w/w) to about 10% (w/w) based on the total weight of the pressurized inhalation composition; (c) citric acid as stabilizer in an amount of from about 0.05% (w/w) to about 0.5% (w/w) based on the total weight of the pressurized inhalation composition; and (d) propellant, wherein the pressurized inhalation composition is in solution form.

In an another embodiment, the present invention relates to a pressurized inhalation composition comprising (a) tiotropium bromide monohydrate in an amount of from about 0.003% (w/w) to about 0.007% (w/w) based on the total weight of the pressurized inhalation composition; (b) ethanol in an amount of from about 1% (w/w) to about 10% (w/w) based on the total weight of the pressurized inhalation composition; (c) citric acid as stabilizer in an amount of from about 0.05% (w/w) to about 0.5% (w/w) based on the total weight of the pressurized inhalation composition; and (d) propellant as HFA134a.

In an another embodiment, the present invention relates to a pressurized inhalation composition comprising (a) tiotropium bromide monohydrate in an amount of from about 0.006% (w/w) based on the total weight of the pressurized inhalation composition; (b) ethanol in an amount of from about 10% (w/w) based on the total weight of the pressurized inhalation composition; (c) citric acid as stabilizer in an amount of about 0.15% (w/w) based on the total weight of the pressurized inhalation composition; and (d) propellant as HFA134a.

In an another embodiment, the present invention relates to a pressurized inhalation composition comprising tiotropium in an amount of from about 0.003% (w/w) to about 0.007% (w/w) based on the total weight of the pressurized inhalation composition, ethanol in an amount of from about 1% (w/w) to about 10% (w/w) based on the total weight of the pressurized inhalation composition, citric acid in an amount of from about 0.05% (w/w) to about 0.5% (w/w) based on the total weight of the pressurized inhalation composition, and HFA134a as a propellant, wherein (i) the metered dose inhaler, upon actuation is configured to provide a fine particle fraction (FPF) of tiotropium of at least 70%, and (ii) metered dose inhaler is configured to deliver about 1 μg, 1.25 μg, 1.5 μg, 2 μg, 2.5 μg, 3 μg, 3.5 μg or 4 μg of tiotropium per actuation.

In an embodiment, the metered dose inhaler delivers about 2 μg, 2.5 μg or 3 μg of tiotropium per actuation.

In an embodiment, the metered dose inhaler delivers about 2.5 μg of tiotropium per actuation.

In an another embodiment, the present invention relates to a pressurized inhalation composition comprising (a) tiotropium bromide in an amount of about 0.006% (w/w) based on the total weight of the pressurized inhalation composition; (b) ethanol in an amount of about 10% (w/w) based on the total weight of the pressurized inhalation composition; (c) citric acid as stabilizer in an amount of about 0.15% (w/w) based on the total weight of the pressurized inhalation composition and (d) a propellant as HFA134a, wherein the composition when administered through a metered dose inhaler delivers about 2.5 μg of tiotropium per actuation.

In an embodiment, the present invention relates to a metered dose inhaler comprising (a) pressurized inhalation composition comprising tiotropium or its pharmaceutically acceptable salt thereof, ethanol, a stabilizer, and a propellant; (b) a canister containing the pressurized inhalation composition; (c) a metering valve; and (d) an actuator optionally connected with a dose counter.

In one of the embodiment, the present invention relates to a metered dose inhaler comprising:

(a) a pressurized inhalation composition comprising tiotropium bromide in an amount of from about 0.0001% (w/w) to about 0.01% (w/w) based on the total weight of the pressurized inhalation composition;

ethanol in an amount of from about 1% (w/w) to about 10% (w/w) based on the total weight of the pressurized inhalation composition; citric acid in an amount of from 0.05% (w/w) to 0.5% (w/w) based on the total weight of the pressurized inhalation composition; and a propellant;

(b) a canister;

(c) a metering valve, and (d) an actuator optionally connected with a dose counter.

In an another embodiment, the present invention relates to a metered dose inhaler comprising (a) a pressurized inhalation composition comprising tiotropium or its pharmaceutically acceptable salt thereof, ethanol, a stabilizer, and a propellant; (b) a canister; (c) a metering valve; and (d) an actuator optionally connected with a dose counter, wherein the actuator has spray orifice diameter of from about 0.15 mm to about 0.3 mm.

In an embodiment, the actuator has spray orifice diameter of about 0.17 to about 0.27 mm.

Yet another embodiment relates to a metered dose inhaler comprising (a) pressurized inhalation composition comprising tiotropium or its pharmaceutically acceptable salt thereof, ethanol, a stabilizer, and a propellant; (b) a canister; (c) a metering valve; (d) an actuator optionally connected with a dose counter, wherein the actuator further has sump volume of about 12 mm$^3$ to about 20 mm$^3$ and/or jet length of about of about 0.30 mm to about 1.0 mm.

Yet another embodiment relates to a metered dose inhaler comprising (a) pressurized inhalation composition comprising tiotropium or its pharmaceutically acceptable salt thereof, ethanol, a stabilizer, and a propellant; (b) a canister; (c) a metering valve; and (d) an actuator optionally connected with a dose counter wherein the actuator further has sump volume of about 15 mm$^3$ to about 18 mm$^3$ and/or jet length of about 0.50 mm to about 1.0 mm.

In an another embodiment, the present invention relates to a metered dose inhaler comprising the pressurized inhalation composition comprising tiotropium or its pharmaceutically acceptable salt thereof, ethanol, a stabilizer, and a propellant, contained in a canister fitted with a metering valve, an actuator optionally connected with a dose counter, wherein the canister used in this invention is made of a metal or metal alloy.

In an another embodiment, the present invention relates to a metered dose inhaler comprising the pressurized inhalation composition comprising tiotropium or its pharmaceutically acceptable salt thereof, ethanol, a stabilizer, and a propellant, contained in a canister fitted with a metering valve, an actuator optionally connected with a dose counter, wherein the canister used in this invention is made of stainless steel (SS) or aluminium.

In an another embodiment, the present invention relates to a metered dose inhaler comprising the pressurized inhalation composition comprising tiotropium or its pharmaceutically acceptable salt thereof, ethanol, a stabilizer, and a propellant, contained in an aluminum canister fitted with a metering valve, an actuator optionally connected with a dose counter, wherein the internal surface of the aluminum canister is coated with either fluorocarbon polymer (FCP) or fluorinated ethylene propylene polymer (FEP).

In an embodiment, the canister is coated with fluorocarbon polymer (FCP).

In an another embodiment, the present invention relates to a metered dose inhaler comprising (a) pressurized inhalation composition comprising tiotropium or its pharmaceutically acceptable salt thereof, ethanol, a stabilizer, and a propellant; (b) a canister; (c) a metering valve; and (d) an actuator optionally connected with a dose counter, wherein the metering valve has one or more sealing gaskets constructed substantially from ethylene propylene diene monomer (EPDM) rubber and has neck gasket constructed from cyclic olefin co-polymer (COCe) rubber.

In another aspect, the present invention relates to a metered dose inhaler comprising (a) pressurized inhalation composition comprising tiotropium bromide, ethanol, citric acid, and a propellant; (b) a canister (c) a metering valve; and (d) an actuator optionally connected with a dose counter, wherein the metered dose inhaler has one or more of (i)-(v) characteristic:

(i) the composition contains tiotropium bromide in dissolved form;

(ii) the composition contains ethanol in an amount of from about 1% (w/w) to about 10% (w/w) based on the total weight of the pressurized inhalation composition and/or citric acid in an amount of from about 0.05% (w/w) to about 0.5% (w/w) based on the total weight of the pressurized inhalation composition;

(iii) the composition is contained into a canister made of stainless steel (SS) or aluminium, wherein the canister is fitted with a metered valve having one or more sealing gaskets constructed substantially from ethylene propylene diene monomer (EPDM) rubber and having a neck gasket constructed from cyclic olefin co-polymer (COCe) rubber;

(iv) an actuator configured to receive the measured dose from the metering valve and to deliver the measured dose, wherein actuator has spray orifice diameter of from about 0.15 mm to about 0.3 mm and/or sump volume of from about 15 mm$^3$ to about 18 mm$^3$ and/or a jet length of from about 0.50 mm to about 1.0 mm; and (v) the metered dose inhaler delivers about 2 μg, 2.5 μg, 3 μg or 3.5 μg of tiotropium per actuation.

In one embodiment, metering valve further comprises pre-ring made up of material selected from polyethylene, polyamide, and polyacetal.

In an another embodiment, the present invention relates to a metered dose inhaler comprising (a) pressurized inhalation composition comprising tiotropium bromide monohydrate in an amount of from about 0.003% (w/w) to about 0.007% (w/w) based on the total weight of the pressurized inhalation composition, ethanol in an amount of from about 1% (w/w) to about 10% (w/w) based on the total weight of the pressurized inhalation composition, citric acid in an amount of from about 0.05% (w/w) to about 0.5% (w/w) based on the total weight of the pressurized inhalation composition, and HFA134a as a propellant, wherein the composition is in solution form; (b) a canister; (c) a metering valve, (d) an actuator optionally connected with a dose counter, wherein the metered dose inhaler delivers about 1 μg, 1.25 μg, 1.5 μg, 2 μg, 2.5 μg, 3 μg, 3.5 μg, or 4 μg of tiotropium per actuation.

In an embodiment, the metered dose inhaler delivers about 2 μg, 2.5 μg, or 3 μg of tiotropium per actuation.

In an embodiment, the metered dose inhaler delivers about 2.5 μg of tiotropium per actuation.

Yet another embodiment, the present invention relates to a pressurized metered dose inhaler composition comprising:

(a) a pressurized inhalation composition comprising tiotropium bromide monohydrate in an amount of from about 0.0001% (w/w) to about 0.01% (w/w) based on the total weight of the pressurized inhalation composition; ethanol in in an amount of from about 1% (w/w) to about 10% (w/w) based on the total weight of the pressurized inhalation composition; citric acid in an amount of from 0.05% (w/w) to 0.5% (w/w) based on the total weight of the pressurized inhalation composition; and HFA134a as propellant, wherein the composition is in solution form;

(b) a canister made of stainless steel (SS) or aluminium, wherein all or part of internal surface of the canister is coated with fluorocarbon polymer (FCP) or fluorinated ethylene propylene polymer (FEP);

(c) a metering valve fitted to the canister, wherein metering valve has one or more sealing gaskets constructed substantially from ethylene propylene diene monomer (EPDM) rubber; and/or has a neck gasket constructed from cyclic olefin co-polymer (COCe) rubber;

(d) an actuator, wherein actuator has spray orifice diameter of from about 0.15 mm to about 0.30 mm; sump volume of from about 15 mm³ to about 18 mm³; and jet length of from about 0.50 mm to about 1.0 mm;

(e) optionally dose counter.

In an embodiment, the amount of tiotropium bromide monohydrate in the present composition is from about 0.001% (w/w) to about 0.01% (w/w), or from about 0.003% (w/w) to about 0.007% (w/w), or from about 0.005% (w/w) to about 0.006% (w/w), based on the total weight of the pressurized inhalation composition.

In one of embodiment, the pressurized inhalation composition comprises tiotropium bromide monohydrate in an amount of about 0.006% (w/w) based on the total weight of the pressurized inhalation composition.

In an embodiment, the amount of ethanol is from about 5% (w/w) to about 10% (w/w) based on the total weight of the pressurized inhalation composition.

In an embodiment, the amount of ethanol is from about 8% (w/w) to about 10% (w/w) based on the total weight of the pressurized inhalation composition.

In an embodiment, the amount of ethanol is about 10% (w/w) based on the total weight of the pressurized inhalation composition.

In an embodiment, the amount of citric acid as present in the composition is from about 0.08% (w/w) to about 0.35% (w/w), or from about 0.1% (w/w) to about 0.2% (w/w) based on the total weight of the pressurized inhalation composition.

In one of embodiment, the pressurized inhalation composition comprises citric acid in an amount of 0.15% (w/w) based on the total weight of the pressurized inhalation composition.

In an embodiment, the pressurized inhalation composition, when tested for Aerodynamic Particle Size Distribution (APSD) (e.g., using an Andersen Cascade Impasto apparatus) after 3 months of storage at 25° C. and 60% relative humidity (e.g., in a crimped canister with metered valve comprised of COCe and/or EPDM gasket), results in a fine particle dose (FPD) for tiotropium or its salt thereof in the range of from about 1 μg to about 3 μg, or from about 1.7 μg to about 2.5 μg, or from about 2 μg to about 2.5 μg.

In an embodiment, the pressurized inhalation composition, when tested for APSD (e.g., using an Andersen Cascade Impasto apparatus) after 3 months of storage at 40° C. and 75% relative humidity (e.g., in a crimped canister with metered valve comprised of COCe and/or EPDM gasket), results in a fine particle dose (FPD) for tiotropium or its salt thereof in the range of from about 1 μg to about 3 μg, or from about 1.7 μg to about 2.5 μg or from about 2 g to about 2.5 μg.

In an embodiment, the pressurized inhaler composition has total impurities in an amount not more than 5%, or not more than 3%, and single maximum impurity not more than 1%, or not more than 0.5%, or not more than 0.2%, when stored at accelerated conditions at 25° C. and 60% RH.

In an embodiment, the pressurized metered dose inhaler wherein the pressurized inhalation composition has total impurities in an amount not more than 5%, or not more than 3%, and single maximum impurity not more than 1%, or not more than 0.5%, or not more than 0.2%, when stored at accelerated conditions at 40° C. and 75% RH.

In an embodiment of any metered dose inhaler, wherein the pressurized inhalation composition provides fine particle dose (FPD) of tiotropium or its salt thereof in the range of from about 1 μg to about 3 μg, or from about 1.7 μg to about 2.5 μg or from about 2 μg to about 2.5 μg.

In an embodiment, the metered dose inhaler provides the fine particle fraction (FPF) of tiotropium or its salt thereof of at least 70% (based upon the delivered dose of each active agent), such as (i) at least 75%, (ii) from about 70% to about 90%, (iii) from about 70% to about 85%, (iv) from about 70% to about 95%, (v) from about 75% and about 95%, (vi) from about 75% to about 85%.

In an embodiment, the metered dose inhaler, wherein the pressurized inhalation composition provides mass median aerodynamic diameter (MMAD) of tiotropium or salt thereof in the range of from about 0.5 μm to about 3 μm, or from about 0.5 μm to about 1.5 m.

In an embodiment, the metered dose inhaler, wherein the pressurized metered composition provides geometric standard deviation (GSD) of tiotropium or its salt thereof in the range of from about 1 μm to about 3.5 μm, or from about 1 μm to about 2.5 μm.

In an embodiment, the pressurized inhalation composition, when administered through a metered dose inhaler provides one or more of the following:

(i) a fine particle dose (FPD) of tiotropium in the range of from about 2 μg to about 2.5 μg;

(ii) a fine particle fraction (FPF) of tiotropium between about 70% and about 85%, In an another embodiment, the preparing a pressurized inhalation composition comprises the following steps:

(i) Preparing a pre-mix solution of ethanol and citric acid;

(ii) Adding tiotropium bromide to the pre-mix solution obtained in step (i);

(iii) Charging propellant into the pre-mix vessel followed by homogenizing the solution;

(iv) Making up the final volume with the propellant;

(v) Crimping the canister with the metered valve; and (vi) Filling the prepared solution obtained in step (iv) into the crimped canister.

Yet another embodiment, the present invention relates to method of treating respiratory disease like Asthma and/or COPD by administering the pressurized inhalation composition as described herein.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the various embodiments of the invention.

DETAILED DESCRIPTION OF THE INVENTION

Figure 1:
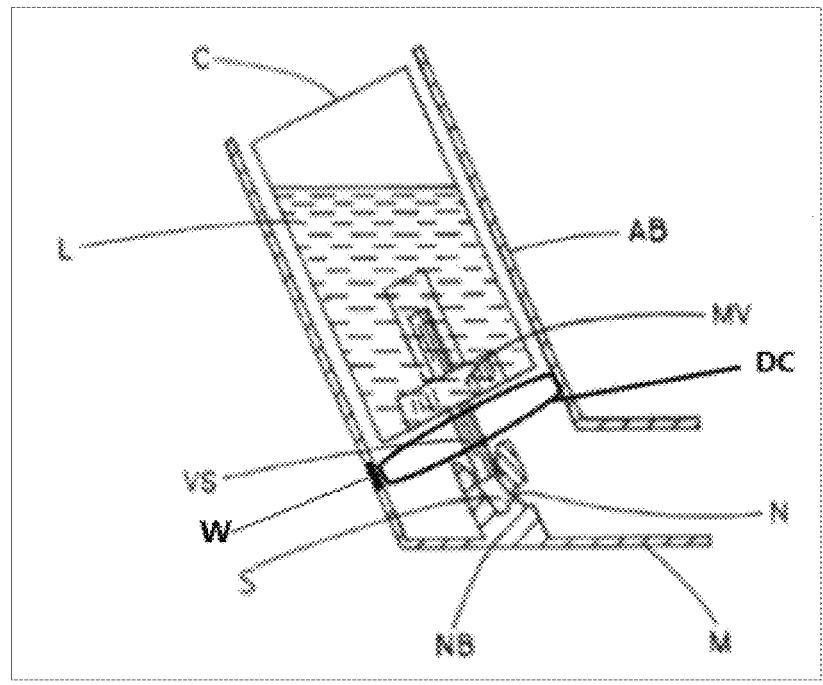
FIG. 1 shows a side view of a MDI, according to an embodiment of the present invention.

The terms used herein are defined as follows. If a definition set forth in the present application and a definition set forth later in a non-provisional application claiming priority from the present provisional application are in conflict, the definition in the non-provisional application shall control the meaning of the terms.

The term singular forms "a," "an" and "the" include plural references unless the context clearly dictates otherwise.

The term "about" as used herein, refers to any value which lies within the range defined by a variation of up to ±15% of the value.

The term "tiotropium" as used herein includes the base form as well as pharmaceutically acceptable salts, solvates, hydrates, its enantiomers, esters, polymorphs, complex, and co-crystals thereof. Pharmaceutically acceptable salts of tiotropium include bromide, bicarbonate, methane sulphonate, benzoate, saccharate, toluenesulfonate which may be present as anhydrate, monohydrates and the like. In a preferred embodiment, tiotropium is present in any of the compositions described herein in the form of a tiotropium bromide monohydrate.

By "salt" or "pharmaceutically acceptable salt", it is meant those pharmaceutically acceptable salts and esters which are, within the scope of sound medical judgment, suitable for use without undue toxicity, irritation, and allergic response, commensurate with a reasonable benefit to risk ratio, and effective for their intended use. The pharmaceutical acceptable salt may be an acid addition salt or an alkali or alkaline earth metal salt.

By "propellant", it is meant a substance used in the form of pressurized gas for production of energy that is subsequently used to create movement of fluid. Propellants comprise the bulk of any MDI formulation and are required to be toxicologically safe, nonflammable, and chemically inert with appropriate boiling points and densities. They are liquefied compressed gas, which function as a driving force and energy source for atomization of the formulation upon actuation. In the present invention, propellant includes HFA134a or HFA227, or a mixture thereof. Preferably, HFA134a is used in this present invention.

The term "metered dose inhaler (MDI)" or "pressurized metered dose inhaler (pMDI)" are interchangeable with each other. The composition in the present invention is pressurized system consisting of a mixture of propellant, ethanol and/or stabilizer and active drug wherein the mixture is released from the delivery device i.e. Metered Dose Inhaler, through a metering valve and stem which fits into the design of an actuator.

The term "Pharmacokinetics (PK)" relates to the study of how the body interacts with administered pressurized inhalation composition for the entire duration of exposure.

The term "Bioequivalence" indicates that the drug products, when given to the same patient in the same dosage regimen, result in equivalent concentrations of drug in plasma and tissues. Bioequivalence is measured by two variables: AUC and Cmax. AUC is the area under the concentration-time curve from zero to infinity. AUC measures the total drug exposure (the extent) across time. Cmax is the maximum (peak) serum concentration that the drug achieves. For two drug products to be said as equivalent both of these variables must match.

The term "Bioequivalent" indicates that drug products, when given to the same patient in the same dosage regimen, have the same therapeutic and adverse effects.

The term "non-pressurized aqueous base inhalation" as used herein the present invention relates to the Soft Mist inhalation solution of tiotropium available under the Brand Name SPIRIVA® Respimat described in U.S. Food & Drug Administration No. 21936. SPIRIVA Respimat composed of inhalation composition containing tiotropium, benzalkonium chloride, disodium edetate, purified water and hydrochloric acid for pH adjustment. SPIRIVA Respimat delivers 5 μg tiotropium as inhalation dose. SPIRIVA Respimat is available in special device which is complex in nature and expensive to the patient.

The term "treating" or "treatment" as used herein also covers the prophylaxis, mitigation, prevention, amelioration, or suppression of a disorder.

The term "respiratory disease or respiratory disorder", in the context of present invention, includes, but is not limited to, asthma, emphysema, bronchitis, COPD, sinusitis, respiratory depression, reactive airways dysfunction syndrome (RADS), acute respiratory distress syndrome (ARDS), irritant induced asthma, occupational asthma, sensory hyperreactivity, airway (or pulmonary) inflammation, multiple chemical sensitivity, and aid in smoking cessation therapy.

The term "stable" meant the composition maintains the physical and chemical integrity of the product. The indicative measures for stability includes fine particle dose (FPD), fine particle fraction (FPF), Mass Median aerodynamic diameter (MMAD), delivered dose (DD) and assay of drug.

The term "inhalation composition" and "pressurized inhalation composition" are interchangeable with each other. It means an inhalation composition which maintains any one or all of the following conditions: (i) the composition maintains the physical and chemical integrity of the product over a period of time such that it is suitable for aerosol inhalation administered by pressurized meter dose inhalers used for delivery of the drug to the respiratory tract, (ii) the composition is capable of substantially maintaining the mass median aerodynamic diameter (MMAD) and the fine particle dose, (iii) the composition does not undergo phase separation by visual observation when stability is tested by shaking the composition (e.g., for 1 minute or shaken once or twice), and in some embodiments, a "stable" pressurized inhalation composition is one in which the fine particle fraction (FPF) or fine particle dose (FPD) of the aerosol does not change more than 15% or between 5-15% in 1 month from the initial FPF or FPD measured at ambient conditions (e.g., about 25° C. and a relative humidity (RH) of about 60%) or at accelerated conditions (e.g., at about 40° C. and about 75% RH).

In another embodiment, a "stable pressurized inhalation composition" is one in which the composition has a total impurity content of not more than 5% or not more than 3% and a single maximum impurity in an amount of not more than 1%, when stored for 6 months at accelerated conditions at 40° C. and 75% RH.

The term % by weight or % w/w refers to percent weight of the component based on the 100% weight of the pressurized inhalation composition.

The term "dose counter" as used herein refers to both dose counter and dose indicator.

The term "fine particle dose" (FPD) is defined as the mass of particles having less than 5 μm in size within the total emitted dose (TED). TED is the mass of drug emitted per actuation that is actually available for inhalation at the mouth.

The term "fine particle fraction" (FPF) is defined as the fine particle dose (FPD) divided by the total emitted dose (TED).

The term "mean mass aerodynamic diameter (MMAD) as used herein means that 50% of particles in the aerodynamic size distribution, based on mass, lie above and below that diameter. This variable is determined according to the Pharmacopoeia (Pharm Eur 2.9.18 Apparatus D, USP 601 Aerodynamic size distribution Apparatus 1) based on measurement with an Anderson cascade impactor. Depending on the aerodynamic particle size the particles are deposited in the lungs at different depths (e.g. in the bronchi, the bronchioles, or the alveoli, etc.). The selected aerodynamic particle size thus serves to control where, in the lungs, the active substance will preferably settle and thus be available.

The Geometric Standard Deviation (GSD) is a measure of the spread of an aerodynamic particle size distribution. Typically, GSD is calculated as follows:

$$GSD = (d_{84}/d_{16})^{1/2}$$

where $d_{84}$ and $d_{16}$ represent the diameters at which 84% and 16% of the aerosol mass are contained, respectively, in diameters less than these diameters.

The fine particle mass (FPM) test is conducted using a validated multistage impactor or impinger method, or a suitably validated alternative. It is considered acceptable to set upper and lower limits on the results of pooled stages corresponding to a particle size distribution of less than 5 μm, although alternative limits may be found acceptable with adequate justification.

The drug mass is reported rather than the percentage of emitted dose (or other derived parameter).

Ethanol concentration can influence the delivery characteristics of metered dose inhalers (MDI) in three ways: (1) by changing the formulation density and thus changing the total mass of formulation atomized during actuation of the device, (2) by changing atomization of the formulation and the size of the atomized droplets, and (3) by changing the evaporation rate of these droplets towards their residual particle sizes. As the concentration of ethanol increases, the vapor pressure of the formulation decreases, this in turn affects the atomization process. The decreased atomization force leads to an increase in the initial droplet size distribution. This results in larger residual particles being present after evaporation of the droplets in the aerosol spray. Additionally, the larger droplets cause increased deposition in the mouth and throat. Thus, increased ethanol concentration leads to a decrease in fine particle fraction (FPF) and fine particle mass (FPM), thereby decreasing the overall dosing efficiency.

The present invention relates to a pressurized inhalation composition in a metered dose inhaler comprising tiotropium or its pharmaceutically acceptable salt thereof, ethanol, a stabilizer, and a propellant.

In one embodiment, wherein the composition in a metered dose inhaler provides a fine particle fraction (FPF) of tiotropium or its pharmaceutically acceptable salt thereof of at least 70%.

In one of the embodiment, the present invention relates to a pressurized inhalation composition in a metered dose inhaler comprising tiotropium or its pharmaceutically acceptable salt thereof, ethanol in an amount of about 1% (w/w) to about 10% (w/w), a stabilizer, and a propellant, wherein the pressurized inhalation composition is pharmacokinetically bioequivalent to non-pressurized aqueous base inhalation formulation of tiotropium.

In an another embodiment, the present invention relates to a pressurized inhalation composition wherein the pharmacokinetic bioequivalence is established by (a) 90% confidence interval for AUC which is between 80% and 125%, and (b) 90% confidence interval for $C_{max}$, which is between 80% and 125%.

In an another embodiment, the present invention relates to a pressurized inhalation composition wherein the $C_{max}$ and AUC of the composition is substantially same as to non-pressurized aqueous base inhalation formulation of tiotropium.

In an embodiment, the pressurized inhalation composition of the present invention is in solution or suspension form. Preferably, the pressurized inhalation composition is in solution form.

Tiotropium as used in the pressurized inhalation composition in the form of tiotropium bromide monohydrate.

The Propellant as used in the pressurized inhalation invention is selected from HFA 134a and HFA 227, or a mixture thereof. HFA 134s may be one the preferred choice by the person skilled in the art.

In another embodiment, the present invention relates to a pressurized inhalation composition wherein the amount of ethanol is in an amount of from about 5% (w/w) to about 10% (w/w), or from about 8% (w/w) to about 10% (w/w) based on the total weight of the pressurized inhalation composition.

In an embodiment, the ethanol is in amount of about 10% (w/w) based on the total weight of the pressurized inhalation composition.

The pharmaceutical composition comprises a stabilizer selected from an organic acid, an inorganic acid (or mineral acid), a surfactant, and a chelating agent.

In an embodiment, the stabilizer is selected from but not limited to citric acid, ascorbic acid, maleic acid, malic acid, hydrochloric acid, phosphoric acid, nitric acid, sulphuric acid, sodium hydroxide, boric acid, sodium citrate, tartaric acid, acetic acid, potassium bicarbonate, potassium citrate, potassium hydroxide, sodium bicarbonate, sodium borate or any combination thereof. Preferably the stabilizer is citric acid as used in this present invention.

In an embodiment, the pressurized inhalation composition is substantially free from water and glycerol.

In another embodiment, the pressurized inhalation composition is substantially free of an anti-oxidant.

In an another embodiment, the pressurized inhalation composition has a pH of from about 2.5 to about 4.0.

The amount of tiotropium bromide monohydrate in the pressurized inhalation composition is in the range of about 0.001% (w/w) to about 0.01% (w/w), or about 0.003% (w/w) to about 0.007% (w/w), or about 0.005% (w/w) to about 0.006%. (w/w) based on the total weight of the pressurized inhalation composition.

In one embodiment, the pressurized inhalation composition comprises tiotropium bromide monohydrate in an amount of about 0.006% (w/w) based on the total weight of the pressurized inhalation composition.

The amount of ethanol in the pressurized inhalation composition is from 5% (w/w) to about 10% (w/w) based on the total weight of the pressurized inhalation composition.

The amount of ethanol in the pressurized inhalation composition is about 8% (w/w) to about 10% (w/w) based on the total weight of the pressurized inhalation composition.

The amount of ethanol in the pressurized inhalation composition is about 10% (w/w) based on the total weight of the pressurized inhalation composition The amount of citric acid in the pressurized inhalation composition is from about 0.08% (w/w) to about 0.35% (w/w), or from about 0.1% (w/w) to about 0.2% (w/w) based on the total weight of the pressurized inhalation composition.

In one embodiment, the pressurized inhalation composition comprises citric acid in an amount of 0.15% (w/w) based on the total weight of the pressurized inhalation composition.

In one embodiment, a pressurized inhalation composition comprises (a) tiotropium bromide monohydrate in amount of from about 0.0001% (w/w) to about 0.01% (w/w) based on the total weight of the pressurized inhalation composition, (b) ethanol in an amount of from about 1% (w/w) to about 10% (w/w) based on the total weight of the pressurized inhalation composition, (c) citric acid in an amount of from 0.05% (w/w) to 0.5% (w/w) based on the total weight of the pressurized inhalation composition, and (d) HFA 134a as a propellant, wherein the pressurized inhalation composition is in solution form.

In an another embodiment, a pressurized inhalation composition comprises (a) tiotropium bromide monohydrate in an amount of from about 0.003% (w/w) to about 0.007% (w/w) based on the total weight of the pressurized inhalation composition; (b) ethanol in an amount of from about 1% (w/w) to about 10% (w/w) based on the total weight of the pressurized inhalation composition; (c) citric acid as stabilizer in an amount of from about 0.05% (w/w) to about 0.5% (w/w) based on the total weight of the pressurized inhalation composition and (d) propellant as HFA134a.

In an another embodiment, a pressurized inhalation composition comprises (a) tiotropium bromide monohydrate in an amount of about 0.006% (w/w) based on the total weight of the pressurized inhalation composition; (b) ethanol in an amount of about 10% (w/w) based on the total weight of the pressurized inhalation composition; (c) citric acid as stabilizer in an amount of about 0.15% (w/w) based on the total weight of the pressurized inhalation composition, and (d) propellant as HFA134a.

In an another embodiment, a pressurized inhalation composition comprises tiotropium bromide monohydrate in an amount of from about 0.003% (w/w) to about 0.007% (w/w) based on the total weight of the pressurized inhalation composition, ethanol in an amount of from about 1% (w/w) to about 10% (w/w) based on the total weight of the pressurized inhalation composition, citric acid in an amount of from about 0.05% (w/w) to about 0.5% (w/w) based on the total weight of the pressurized inhalation composition, and HFA134a as a propellant, wherein (i) the metered dose inhaler, upon actuation is configured to provide a fine particle fraction (FPF) of tiotropium of at least 70%, and (ii) metered dose inhaler is configured to deliver about 1 µg, 1.25 µg, 1.5 µg, 2 µg, 2.5 µg, 3 µg, 3.5 µg or 4 µg of tiotropium per actuation.

In an embodiment, the metered dose inhaler delivers about 2 µg, 2.5 µg, or 3 µg of tiotropium per actuation.

In an embodiment, the metered dose inhaler delivers about 2.5 µg of tiotropium per actuation.

In an another embodiment, a pressurized inhalation composition comprises (a) tiotropium bromide monohydrate in an amount of about 0.006% (w/w) based on the total weight of the pressurized inhalation composition; (b) ethanol in an amount of about 10% (w/w) based on the total weight of the pressurized inhalation composition; (c) citric acid as stabilizer in an amount of about 0.15% (w/w) based on the total weight of the pressurized inhalation composition, and (d) propellant as HFA134a, wherein the pressurized inhalation composition, when administered through a metered dose inhaler, delivers about 2.5 µg of tiotropium per actuation.

In yet another embodiment, a drug delivery device comprises a pressurized inhalation composition as described herein. The drug delivery device is designed to administer a pressurized aerosol inhalation composition to the lungs. A particularly preferred drug delivery device is a metered dose inhaler. The drug delivery device comprises a suitable aerosol canister, provided with a metering valve, containing a pressurized inhalation composition of the present invention and an actuator housing adapted to hold the canister and allow for drug delivery. The canister in the drug delivery device has a head space representing greater than about 15% of the total volume of the canister. Furthermore, the pressurized inhalation composition does not clog any part of the drug delivery device, e.g., valve.

In an embodiment, a metered dose inhaler (MDI) of the present invention is shown in FIG. 1, and includes an Actuator, or Actuator Body AB in which is positioned a Canister C. Canister C contains a Liquid medicament L in solution with a propellant. The propellants include HFA-134a or HFA-227. The canister possesses a Metering Valve MV for measuring discrete doses of the drug formulation fluid. A Valve Stem VS extends from the metering valve and acts as a conduit to pass the metered dose into a Nozzle Block NB situated in the actuator body, in which the valve stem is seated. The nozzle block has a passageway extending through it that forms an Expansion Chamber/Sump S in which the propellant formulation expands. A Nozzle channel N, which is aligned with a Mouthpiece opening M, exits the Expansion Chamber/Sump S, approximately tangential to the longitudinal axis of the axis of the valve stem. To use this type of MDI, the patient places the mouthpiece against their lips and actuates the MDI by depressing the canister into the actuator body AB. Upon actuation, a metered dose is measured by the metering valve MV and is expelled from the valve stem VS. The expelled dose passes into and through the Expansion Chamber/Sump S of the nozzle block NB and exits the nozzle block NB from the Nozzle channel N. A patient inhales through the mouthpiece opening M upon the release of the metered dose and inhales the drug dose as it exits the MDI.

Figure 2:
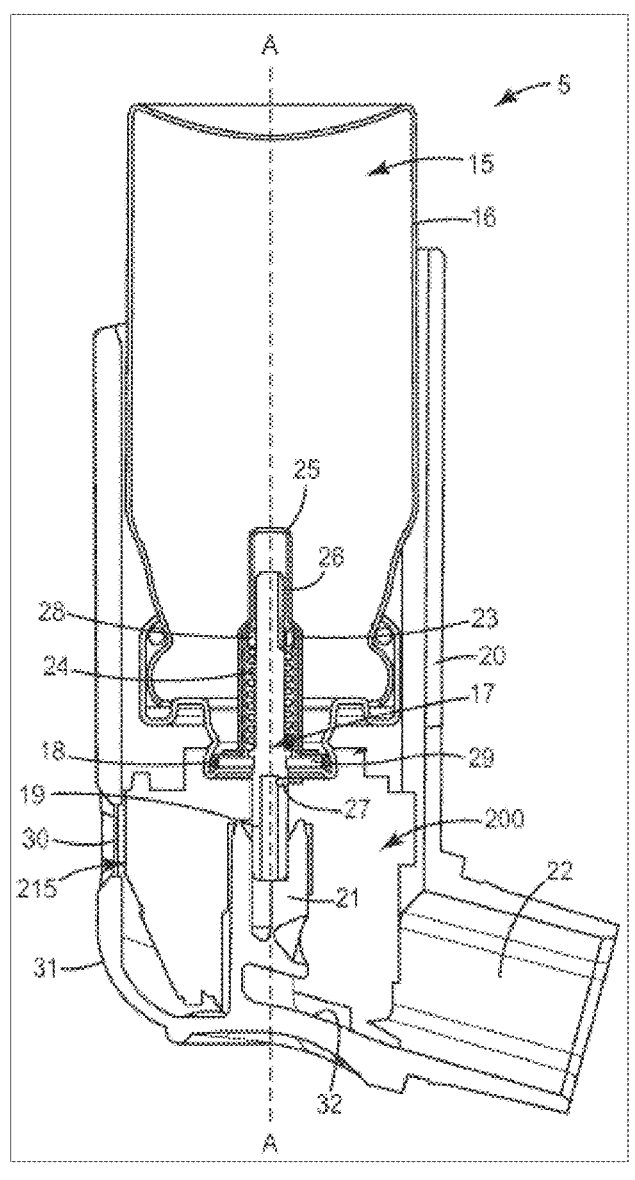
FIG. 2 shows a vertical cross section of a MDI, according to an embodiment of the present invention.

In one of the embodiment of the present invention, FIG. 2 shows a vertical cross-section through a Metered Dose Inhaler (5). The Metered Dose Inhaler (5) comprises the following components: a canister (15), an actuator (20) and optionally a dose counter (200). The dose counter (200) is shown diagrammatically with its outer profile in an outline form. The canister (15) includes an aerosol container (16) equipped with a metering valve (17) secured via a ferrule (18). The metering valve (17) includes, inter alia, a valve stem (19), generally a valve body (23) defining a metering chamber, and a spring (24). The metering valve (17) may also include an outer valve body (25) serving as a bottle emptier and/or as defining a pre-metering chamber. The container (16) contains a pressurized metered dose composition of tiotropium and a propellant selected from HFA 227 and HFA 134a. The actuator (20) and canister (15) are arranged so that the valve stem (19) engages with a nozzle block (21) provided within the actuator (20) so that the canister (15) is thus retained in the actuator (20). The user actuates the pressurized metered dose inhaler (5) to dispense a single dose of tiotropium via the mouthpiece (22) by pressing down on the container (16) (referred to as an actuation stroke). Due to the fact that the valve stem (19) is held fixed by the nozzle block (21), and the aerosol container (16) moves downwardly when the user presses down on it (thus compressing the valve spring (24)), there is a relative reciprocal movement between the valve stem (19) and the aerosol container (16). On this actuation (outward) stroke, once the aerosol container (16) moves sufficiently downwards, an inner groove (26) of the valve stem (19) is completely passed by an inner gasket seal (28), so that the metering chamber, defined by the valve body (23), is sealed off, and once the aerosol container (16) moves further sufficiently downwards, an opening (27) of an outer portion of the valve stem (19) is passed by an outer gasket (29), resulting in communication of the opening (27) with the metering chamber, defined by the valve body (23), so that the metering valve (17) will fire (dispense) a metered dose of tiotropium (i.e. that quantity of formulation in the metering chamber). After actuation, once the user releases the aerosol container (16), the aerosol container (16), on its return stroke, will move (under the force of the expansion of the spring (24)) upwardly, relative to the valve stem, back to its position of rest. A bottom floor (32) of the actuator (20) provides a base for fitting of the dose counter (200). A longitudinal axis of reciprocal movement, between the metering valve, defined by the valve body (23), and the aerosol container (16) is labelled "A" (i.e. the first axis and also sometimes referred to as the actuation axis). As illustrated, the dose counter (200) is mounted within the interior of the actuator (20), generally positioned beneath the aerosol container (16), near and around the nozzle block (21). As shown in FIG. 2, the dose counter (200) may be provided with a window (215) to allow sight of indicia, where the indicia may be viewed through a window (30) in an actuator back wall (31). The dose counter (200), once mounted, desirably remains in position within the actuator (20), even when the aerosol canister (15) is removed, so that the dose counter (200) may not be removed by the user of the inhaler (5). The dose counter (200) is positioned around a nozzle block (21) of the actuator (20).

The Metered Dose Inhaler (5) comprises a suitable aerosol canister (16) with a metering valve (17) containing a pressurized metered dose inhalation composition and an actuator (20) adapted to hold the aerosol canister (16) and allow for drug delivery.

The invention relates to a metered dose inhaler comprising (a) pressurized inhalation composition comprising tiotropium or its pharmaceutically acceptable salt thereof, ethanol, a stabilizer, and a propellant; (b) a canister; (c) a metering valve, and (d) an actuator optionally connected with a dose counter. The canister contains approximately 30, 60, or 120 actuations or fewer, preferably about 60 actuations (i.e. a one-month supply, based on two actuations per dose). However, even in this more challenging environment, the formulation of the present invention is able to provide the required level of chemical stability. The canister may be made of any suitable material such as aluminium, aluminium alloys, stainless steel, tin, plastic or glass which may be coated or uncoated. Some drugs tend to adhere to the inner surfaces, i.e., walls of the canister and may clog metering valves of the device components. This can lead to the patient getting significantly less than the prescribed amount of the active agent upon each actuation of the MDI. Coating the inner surface of the container with a suitable polymer can reduce this adhesion problem. Suitable coatings include fluorocarbon copolymers such as FEP-PES (fluorinated ethylene propylene and polyethersulphone) and PFA-PES (perfluoroalkoxyalkane and polyethersulphone), epoxy and ethylene. Alternatively, the inner surfaces of the canister may be anodized, plasma treated or plasma coated. According to a one of the embodiment of the present invention, the pMDI comprises a canister composed of metal or metal alloy. In an embodiment, pMDI comprises a canister composed of aluminium in which the internal surfaces are coated with either fluorocarbon polymer (FCP) or fluorinated ethylene propylene (FEP) polymer. Preferably, fluorocarbon polymer (FCP) coated canister is used in this invention. Stainless Steel canisters are well known in the art, hence may be used in the present invention. The canister is fitted with a valve, preferably a metering valve.

Metering valves suitable to deliver a specific amount of the composition each time the device is actuated. Metering valve also aid in minimizing propellant evaporation and moisture ingress. Once a valve is crimped into place, the canisters must be able to adequately seal the propellant without leaking. A suitable gasket is used between the valve and the canister to prevent degradation of the product and/or to prevent leakage of the composition. A suitable gasket also helps in reducing the leachable volume of the composition inside the packaging. Preferably, the gasket used is made up of butyl rubber or polymer gasket selected from EPDM or cyclic olefin co-polymer. The suitable metering valve has at least cyclic olefin co-polymer gasket and at least one pre-ring. At least one pre-ring is preferred as it assists in reducing the moisture absorption inside the packaging. A suitable pre-ring also helps in preventing the leakage during storage or transportation of the meter dose inhaler product. The valve used herein is preferably a 25-63 microlitre valve, more preferably a 25 or 50 microlitre valve having one or more sealing gasket constructed substantially from ethylene propylene diene monomer (EPDM) rubber, neck gasket constructed from cyclic olefin co-polymer (COCe) rubber and pre-ring made up of material selected from polyethylene, polyamide and polyacetal.

In one embodiment, an actuator with a spray orifice diameter of about 0.15 mm to about 0.3 mm may be used in the invention. The choice of actuator plays an important role in drug delivery which in turn is dependent on various parameters like spray orifice diameter, jet length, stem block, sump geometry, sump volume and the like. In one of the embodiment, an actuator with a spray orifice diameter of about 0.17 mm to about 0.27 mm is used in the present invention.

A sump is generally located in a valve stem block adjacent to an actuator outlet. These sumps have angles and corners where the medicament being delivered can accumulate and/or deposit, giving rise to a reduction in the dose available and/or an increase in occurrence of blockage of a spray orifice. According to the present invention, the Sump S has an internal volume or sump volume smaller than 20 mm$^3$ and larger than 12 mm$^3$. The actuator used herein for dispensing the drug delivers the volume of about 45 μl-65 μl per actuation or administration. Patient may use one or two puffs once or twice daily as per the requirement or severity of disease.

According to present invention, the actuator used herein has one or more of following features:

(a) a spray orifice diameter of from about 0.15 mm to about 0.3 mm;

(b) a sump volume of from about 15 mm$^3$ to about 18 mm$^3$;

(c) a jet length of from about 0.5 mm to about 1.0 mm;

In an another embodiment, the present invention relates to a metered dose inhaler comprising (a) a pressurized inhalation composition comprising tiotropium or its pharmaceutically acceptable salt thereof, ethanol, a stabilizer, and a propellant; (b) a canister; (c) a metering valve, and (d) an actuator optionally connected with dose counter, wherein the metered dose inhaler delivers about 1 μg, 1.25 μg, 1.5 μg, 2 μg, 2.5 μg, or 3 μg, or 3.5 μg, or 4 μg of tiotropium per actuation. Preferably, the metered dose inhaler delivers about 2 μg, 2.5 μg, 3 μg, or 3.5 μg of tiotropium per actuation.

The present invention relates to a metered dose inhaler comprising (a) a pressurized inhalation composition comprising tiotropium bromide, ethanol, citric acid as a stabilizer, and a propellant; (b) a canister; (c) a metering valve; and (d) an actuator optionally connected with a dose counter, wherein the metered dose inhaler has one or more of (i)-(v) characteristics:

(i) the pressurized inhalation composition comprises tiotropium bromide in dissolved form;

(ii) the pressurized inhalation composition comprises ethanol in an amount of from about 1% (w/w) to about 10% (w/w) based on the total weight of the pressurized inhalation composition and/or citric acid in an amount of from about 0.05% (w/w) to about 0.5% (w/w) based on the total weight of the pressurized inhalation composition;

(iii) the pressurized inhalation composition is contained in a canister made from stainless steel (SS) or aluminium wherein the canister is fitted with a metered valve having one or more sealing gasket constructed substantially from ethylene propylene diene monomer (EPDM) rubber and having a neck gasket constructed from cyclic olefin co-polymer (COCe) rubber.

(iv) an actuator configured to receive the measured dose from the metering valve and to deliver the measured dose, wherein actuator has spray orifice diameter of from about 0.17 mm to about 0.27 mm and/or sump volume of from about 15 mm$^3$ to about 18 mm$^3$ and/or jet length of from about 0.50 mm to about 1.0 mm.

(v) the metered dose inhaler delivers about 2 μg, 2.5 μg, 3 μg, or 3.5 μg of tiotropium per actuation.

In an embodiment, the internal surface of the aluminum canister is coated with either fluorocarbon polymer (FCP) or fluorinated ethylene propylene polymer (FEP). Preferably, a FCP coated aluminium canister is used in this invention.

The metering valve used in this invention further comprises pre-ring made up of material selected from polyethylene, polyamide, and polyacetal.

Another embodiment, the present invention relates to a metered dose inhaler (MDI) composition comprising:

(a) a pressurized inhalation composition comprising tiotropium bromide monohydrate in an amount of from 0.003% (w/w) to 0.007% (w/w) based on the total weight of the pressurized inhalation composition; ethanol in an amount of from about 1% (w/w) to about 10% (w/w) based on the total weight of the pressurized inhalation composition; citric acid as a stabilizer in an amount of from about 0.05% (w/w) to 0.5% (w/w) based on the total weight of the pressurized inhalation composition; and a propellant, wherein the composition is in solution form;

(b) a canister;

(c) a metering valve fitted to the canister; and (d) an actuator optionally connected with dose counter.

Yet another embodiment, the present invention relates to a metered dose inhaler (MDI) comprising:

(a) a pressurized inhalation composition comprising tiotropium bromide in an amount of from 0.0001% (w/w) to 0.01% (w/w) based on the total weight of the pressurized inhalation composition; ethanol in amount of from about 1% (w/w) to about 10% (w/w) based on the total weight of the pressurized inhalation composition; citric acid as a stabilizer in an amount of from 0.05% (w/w) to 0.5% (w/w) based on the total weight of the pressurized inhalation composition; and a propellant, wherein the composition is in solution form;

(b) a canister made of a metal or metal alloy selected from stainless steel (SS) or aluminium, wherein all or part of internal surface of the canister is coated with fluorocarbon polymer (FCP) or fluorinated ethylene propylene polymer (FEP);

(c) a metering valve fitted to the canister, wherein the metering valve has one or more sealing gaskets constructed substantially from ethylene propylene diene monomer (EPDM) rubber; and (d) an actuator, wherein the actuator has spray orifice diameter of from about 0.15 mm to about 0.30 mm; a sump volume of from about 15 mm$^3$ to about 18 mm$^3$; and a jet length of from about 0.50 mm to about 1.0 mm.

(e) optionally a dose counter.

Yet another embodiment, the metered dose inhaler delivers about 1 μg, 1.25 μg, 1.5 μg, 2 μg, 2.5 μg, 3 μg, 3.5 μg, or 4 μg of tiotropium per actuation. Preferably, the metered dose inhaler delivers about 2 μg, 2.5 μg, 3 μg, or 3.5 μg of tiotropium per actuation.

In one embodiment, the pressurized inhalation composition, when tested for APSD (e.g., using an Andersen Cascade Impasto apparatus) after 3 months of storage at 25° C. and 60% relative humidity (e.g., in a crimped canister with metered valve comprised of COCe and/or EPDM gasket), results in a fine particle dose for tiotropium or its salt thereof in the range of from about 1 μg to about 3 μg or from about 1.7 μg to about 2.5 μg or from about 2 μg to about 2.5 μg.

In another embodiment, the pressurized inhalation composition, when tested for APSD (e.g., using an Andersen Cascade Impactor apparatus) after 3 months of storage at 40° C. and 75% relative humidity (e.g., in a crimped canister with metered valve comprised of CoCe and/or EPDM gasket) results in a fine particle dose for tiotropium or its salt thereof of from about 1 μg to about 3 μg or from about 1.7 μg to about 2.5 μg or from about 2 μg to about 2.5 μg.

In an embodiment, the pressurized inhaler composition has total impurities in an amount not more than 5% or not more than 3%, and single maximum impurity not more than 1% or not more than 0.5% or not more than 0.2% when stored at accelerated conditions at 25° C. and 60% RH.

In an embodiment, the pressurized inhaler composition has total impurities in an amount not more than 5% or not more than 3%, and single maximum impurity not more than 1% or not more than 0.5% or not more than 0.2% when stored at accelerated conditions at 40° C. and 75% RH.

In one embodiment of any of the pressurized inhalation compositions provides fine particle dose (FPD) of tiotropium or its salt thereof in the range of from about 1 μg to about 3 g or from about 1.7 μg to about 2.5 μg or from about 2 μg to about 2.5 μg.

In one embodiment, any of the pressurized inhalation compositions provides the fine particle fraction (FPF) of tiotropium or its salt thereof between about 30% and about 100% (based upon the delivered dose of each active agent), such as between about 45% and about 90%, or between about 70% and about 85%.

In one embodiment, any of the pressurized inhalation compositions provides mass median aerodynamic diameter (MMAD) of tiotropium or its salt thereof in the range of about 0.5 μm to about 3 μm or about 0.5 μm to about 1.5 μm.

In one embodiment, any of the pressurized inhalation compositions provides geometric standard deviation (GSD) of tiotropium or its salt thereof in the range of about 1 μm to about 3.5 μm or about 1 μm to about 2.5 μm.

In an embodiment, the pressurized inhalation composition of the present invention is contained in a canister provided with a metering valve having at least a butyl rubber or EPDM or a cyclic olefin co-polymer gasket and/or at least one pre-ring to prevent the degradation of the product and/or to prevent the leakage of product contained in the canister during storage or transportation. A suitable gasket and presence of at least one pre-ring helps in reducing the moisture absorption and leachable volume of the composition. The pre-ring is made up of material selected from polyethylene, polyamide, and polyacetal.

In a further embodiment, a metered dose inhaler may additionally comprise of either a dose indicator or a dose counter.

In an another embodiment, the present invention relates to a process of preparing a pressurized inhalation composition wherein the process comprises the following steps:

(i) Preparing a pre-mix solution of ethanol and citric acid;

(ii) Adding tiotropium bromide to the pre-mix solution obtained in step (i);

(iii) Charging propellant into the pre-mix vessel followed by homogenizing the solution;

(iv) Making up the final volume with the propellant;

(v) Crimping the canister with the metered valve;

(vi) Filling the prepared solution obtained in step (iv) into the crimped canister.

Yet another embodiment, the present invention relates to method of treating respiratory disease like Asthma and/or COPD by administering the pressurized inhalation composition as described herein.

In a preferred embodiment, the pressurized inhalation composition is administered to a subject in need at least once or at least twice daily. Preferably once daily.

It will be understood that various modifications may be made to the embodiments disclosed herein. Therefore, the above description should not be construed as limiting, but merely as exemplifications of preferred embodiments. Other arrangements and methods may be implemented by those skilled in the art without departing from the scope and spirit of this invention.

The following examples are provided to enable one skilled in the art to practice the invention and are merely illustrative of the invention. The examples should not be construed to limit the scope of the invention.

Examples (A) Composition:

TABLE 1a

| Test Examples: Tiotropium MDI Composition (High strength) | | | | |
|---|---|---|---|---|
| Sr. | | Quantity (% w/w) | | |
| No. | Ingredients | Ex. (i) | Ex. (ii) | Ex. (iii) | Ex. (iv) |
| 1. | Tiotropium Bromide Monohydrate | 0.00585 | 0.005850 | 0.005850 | 0.005850 |
| 2. | Ethanol | 8 | 10 | 12 | 15 |
| 3. | Citric acid | 0.15 | 0.15 | 0.15 | 0.15 |
| 4. | HFA134a | 91.8441 | 89.8441 | 87.8441 | 84.8442 |

20

TABLE 1b

| Test Examples: Tiotropium MDI Composition (Low strength) | | |
|---|---|---|
| Sr. | | Quantity (% w/w) |
| No. | Ingredients | Ex. (v) |
| 1. | Tiotropium Bromide Monohydrate | 0.002923 |
| 2. | Ethanol | 10 |
| 3. | Citric acid | 0.15 |
| 4. | HFA134a | 89.8471 |

Manufacturing Procedure:

1. Preparing a pre-mix solution of ethanol and citric acid.
2. Adding tiotropium bromide to the pre-mix solution obtained in step (1).
3. Charging propellant HFA134a into the pre-mix vessel followed by homogenizing the solution.
4. Making up the final volume with propellant.
5. Crimping the canister with the metered valve.
6. Filling the prepared solution obtained in step (4) into the crimped canister.

TABLE 2

| APSD and Assay Data for Test Examples-Tiotropium MDI (High strength) | | | | |
|---|---|---|---|---|
| | Values | | | |
| Parameters | Ex. (i) | Ex. (ii) | Ex. (iii) | Ex. (iv) |
| FPD (µg) | 2.272 | 2.017 | 1.97 | 1.55 |
| FPF (%) | 82.666 | 79.239 | 69.70 | 64.33 |
| MMAD (µm) | 1.159 | 0.991 | 0.98 | 1.20 |
| GSD (µm) | 1.721 | 1.949 | 1.53 | 1.88 |

(B) Method of Treatment:

Following Pharmacokinetic Study of the metered dose inhaler of the present invention in Healthy Adult Male Human Subject is being conducted. A Comparative, Open Label, Randomized, Single Inhaled Dose (5 mcg), Fully Replicated Crossover Study to Evaluate the Relative Bioavailability of Test Formulation of Tiotropium Pressurised Inhalation Aerosol with Spiriva® Respimat® Inhalation Solution of Boehringer Ingelheim Pharma GmbH, Deutschland Under Fasting Condition.

The objective of planned study is to evaluate the relative bioavailability of single inhaled dose 5 mcg of test formulation, Tiotropium Pressurised Inhalation Aerosol and Spiriva Respimat® Inhalation Solution under fasting condition.

Following parameters is to be evaluated during Pharmacokinetic study: Cmax, Tmax, $AUC_{0-t}$, $AUC_{0-\infty}$, Pharmacokinetic Study Results

TABLE 3

| Descriptive Statistics of Tiotropium (N = 23) | | |
|---|---|---|
| | Arithmetic Means (±SD) | |
| Pharmacokinetic Parameters | Test Product | Reference Product |
| Cmax (pg/mL) | 6.963 ± 3.8817 | 6.609 ± 3.7462 |
| AUC(0-0.5 hrs) (pg · hr/mL) | 1.894 ± 0.9801 | 1.898 ± 0.7855 |
| AUC(0-t) (pg · hr/mL) | 38.688 ± 13.1754 | 42.138 ± 9.9997 |
| AUC(0-∞) (pg · hr/mL) | 70.602 ± 22.5249 | 79.386 ± 29.4017 |

Median (range)

TABLE 4

| | | | | | | Widened Limits for Confidence Interval based on reference variability | |
|---|---|---|---|---|---|---|---|
| | Least Square Means | | | 90% Confidence | | | |
| | Test | Reference | Ratio | Intervals | | | |
| Parameter | T | R | (%) | Lower | Upper | Lower | Upper |
| $C_{max}$ (pg/mL) | 5.87 | 5.77 | 101.80 | 89.14 | 116.26 | 80.00 | 125.00 |
| $AUC_{(0-0.5\ hrs)}$ (pg · hr/mL) | 1.63 | 1.72 | 94.61 | 83.89 | 106.71 | 80.00 | 125.00 |
| $AUC_{(0-t)}$ (pg · hr/mL) | 35.76 | 40.06 | 89.26 | 83.21 | 95.75 | 80.00 | 125.00 |

Summary Statistics of Tiotropium

From the above results, under the Fasting condition, the ratio of geometric least square means of test and reference formulation for ln-transformed pharmacokinetic parameter Cmax, AUC(0-0.5 hrs) and AUC(0-t) of Tiotropium were 101.80%, 94.61% and 89.26% respectively while two one sided 90% confidence intervals for Cmax were 89.14-116.26%, AUC(0-0.5 hrs) were 83.89-106.71% and for AUC(0-t) were 83.21-95.75% demonstrating equivalent exposure. Hence, objective of the study was achieved.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described above.

All publications, patents, and patent applications cited in this application are herein incorporated by reference to the same extent as if each individual publication, patent, or patent application was specifically and individually indicated to be incorporated herein by reference.

The invention claimed is:

1. A pressurized inhalation composition in a metered dose inhaler comprising:
    tiotropium bromide monohydrate in an amount of from about 0.003% (w/w) to about 0.007% (w/w), based on the total weight of the pressurized inhalation composition,
    ethanol in an amount of about 10% (w/w), based on the total weight of the pressurized inhalation composition,
    a stabilizer in an amount of from about 0.05% (w/w) to about 0.5% (w/w), based on the total weight of the pressurized inhalation composition, and
    propellant, wherein
        the metered dose inhaler comprises a canister, a metering valve, and an actuator, the actuator having a spray orifice diameter of from about 0.15 mm to about 0.3 mm,
        the metered dose inhaler, upon actuation, is configured to provide a fine particle fraction (FPF) of tiotropium of at least 70%, and
        the metered dose inhaler is configured to deliver about 1 µg, 1.5 µg, 2 µg, 2.5 µg, 3 µg, 3.5 µg, or 4 µg of tiotropium per actuation.

2. The pressurized inhalation composition of claim 1, wherein the metered dose inhaler is configured to deliver about 2 µg, 2.5 µg, or 3 µg of tiotropium per actuation.

3. The pressurized inhalation composition of claim 2, wherein the metered dose inhaler is configured to deliver about 2.5 µg of tiotropium per actuation.

4. The pressurized inhalation composition of claim 1, wherein:
    the tiotropium bromide monohydrate is in an amount of about 0.006% (w/w), based on the total weight of the pressurized inhalation composition,
    the stabilizer is citric acid in an amount of about 0.15% (w/w), based on the total weight of the pressurized inhalation composition,
    the propellant is HFA134a, and
    the metered dose inhaler is configured to deliver about 2.5 µg of tiotropium per actuation.

5. The pressurized inhalation composition of claim 1 used for the treatment of asthma and/or chronic obstructive pulmonary disease (COPD).

6. The pressurized inhalation composition of claim 1, wherein the metered dose inhaler further comprises a dose counter connected to the actuator.

7. The pressurized inhalation composition of claim 1, wherein the actuator has spray orifice diameter of from about 0.17 mm to about 0.27 mm.

8. The pressurized inhalation composition of claim 7, wherein the actuator has a sump volume of from about 12 mm³ to about 20 mm³ and a jet length of from about 0.30 mm to about 1.0 mm.

9. The pressurized inhalation composition of claim 8, wherein the sump volume is from about 15 mm³ to about 18 mm³, and the jet length is from about 0.50 mm to about 1.0 mm.

10. The pressurized inhalation composition of claim 1, wherein the canister is made of a metal or metal alloy.

11. The pressurized inhalation composition of claim 10, wherein the metal or metal alloy is a stainless steel (SS) or aluminium.

12. The pressurized inhalation composition of claim 10, wherein an internal surface of the canister is at least partially coated with a fluorocarbon polymer (FCP) or a fluorinated ethylene propylene polymer (FEP).

13. The pressurized inhalation composition of claim 1, wherein the metering valve comprises:
    one or more sealing gaskets made substantially of ethylene propylene diene monomer (EPDM) rubber; and/or
    a neck gasket made of a cyclic olefin co-polymer (COCe) rubber.

14. The pressurized inhalation composition of claim 1, wherein:
    the tiotropium bromide monohydrate is in an amount of about 0.006% (w/w), based on the total weight of the pressurized inhalation composition,

the ethanol is in an amount of about 10% (w/w), based on the total weight of the pressurized inhalation composition, the stabilizer is citric acid in an amount of about 0.15% (w/w), based on the total weight of the pressurized inhalation composition, and the propellant is HFA134a.

15. The pressurized inhalation composition of claim 14, wherein the metered dose inhaler provides one or more of following:

(i) a fine particle dose of tiotropium in the range of about 2.0 µg to about 2.5 µg; and (ii) a fine particle fraction (FPF) of tiotropium between 70% and about 85%.

16. A pressurized inhalation composition in a metered dose inhaler comprising:

tiotropium or a pharmaceutically acceptable salt thereof, ethanol in an amount of about 10% (w/w), based on the total weight of the pressurized inhalation composition, a stabilizer, and a propellant, wherein the metered dose inhaler comprises a canister, a metering valve, and an actuator, the actuator having a spray orifice diameter of from about 0.15 mm to about 0.3 mm, the metered dose inhaler, upon actuation, is configured to provide a fine particle fraction (FPF) of tiotropium or a pharmaceutically acceptable salt thereof of at least 70%, and administration of about 5 µg of the pressurized inhalation composition to a patient provides a $C_{max}$ of 6.963±3.8817 pg/mL.

17. The pressurized inhalation composition of claim 16, wherein the metered dose inhaler, upon actuation, is configured to provide a fine particle fraction (FPF) of tiotropium or a pharmaceutically acceptable salt thereof of between 70% and about 85%.

18. The pressurized inhalation composition of claim 16, wherein the pressurized inhalation composition is pharmacokinetically bioequivalent to a non-pressurized aqueous base inhalation formulation of tiotropium approved by the U.S. Food and Drug Administration under New Drug Application No. 21936, where the pharmacokinetic bioequivalence is established by (a) 90% confidence interval for AUC, which is between 80% and 125%, and (b) 90% confidence interval for $C_{max}$, which is between 80% and 125%.

19. The pressurized inhalation composition of claim 16, wherein the pressurized inhalation composition is in solution form.

20. The pressurized inhalation composition of claim 16, wherein the pressurized inhalation composition comprises tiotropium bromide monohydrate.

21. The pressurized inhalation composition of claim 20, wherein the tiotropium bromide monohydrate is in an amount of from about 0.001% (w/w) to about 0.01% (w/w), based on the total weight of the pressurized inhalation composition.

22. The pressurized inhalation composition of claim 16, wherein the propellant is selected from the group consisting of HFA134a, HFA227, and any mixture thereof.

23. The pressurized inhalation composition of claim 16, wherein the weight ratio of the ethanol to the stabilizer is from about 100:1 to about 2:1.

24. The pressurized inhalation composition of claim 16, wherein the stabilizer is selected from the group consisting of citric acid, ascorbic acid, maleic acid, malic acid, hydrochloric acid, phosphoric acid, nitric acid, sulphuric acid, and any mixture thereof.

25. The pressurized inhalation composition of claim 24, wherein the stabilizer is citric acid present in an amount of from about 0.05% (w/w) to about 0.5% (w/w), based on the total weight of the pressurized inhalation composition.

26. The pressurized inhalation composition of claim 16, wherein:

the pressurized inhalation composition is substantially free of water, glycerol, and anti-oxidant, and the pH of the pressurized inhalation composition is from about 2.5 to about 4.0.

27. The pressurized inhalation composition of claim 20, wherein:

the tiotropium bromide monohydrate is in an amount of about 0.006% (w/w), based on the total weight of the pressurized inhalation composition, the ethanol is in an amount of about 10% (w/w), based on the total weight of the pressurized inhalation composition, the stabilizer is citric acid in an amount of about 0.15% (w/w), based on the total weight of the pressurized inhalation composition, and the propellant is HFA134a.

28. The pressurized inhalation composition of claim 16, wherein the metered dose inhaler, upon actuation, is configured to provide a fine particle fraction (FPF) of tiotropium or a pharmaceutically acceptable salt thereof of greater than 75%.

29. The pressurized inhalation composition of claim 1, wherein the metered dose inhaler, upon actuation, is configured to provide a fine particle fraction (FPF) of tiotropium or a pharmaceutically acceptable salt thereof of greater than 75%.

30. A pressurized inhalation composition in a metered dose inhaler comprising:

tiotropium bromide monohydrate in an amount of about 0.006% (w/w), based on the total weight of the pressurized inhalation composition, ethanol in an amount of about 10% (w/w), based on the total weight of the pressurized inhalation composition, citric acid in an amount of about 0.15% (w/w), based on the total weight of the pressurized inhalation composition, and HFA134a propellant, wherein the metered dose inhaler comprises a canister, a metering valve, and an actuator, the actuator having a spray orifice diameter of from about 0.17 mm to about 0.27 mm, the metered dose inhaler, upon actuation, is configured to provide a fine particle fraction (FPF) of tiotropium of at least 70%, the metered dose inhaler is configured to deliver about 2.5 µg per actuation, and administration of about 5 µg of the pressurized inhalation composition to a patient provides a $C_{max}$ of 6.963±3.8817 pg/mL or an AUC(0-0.5 hrs) of 1.894±0.9801 pg·hr/mL.

* * * * *